(12) United States Patent
Horvath et al.

(10) Patent No.: US 7,365,083 B2
(45) Date of Patent: Apr. 29, 2008

(54) AMIDE DERIVATIVES AS NMDA RECEPTOR ANTAGONISTS

(75) Inventors: Csilla Horvath, Budapest (HU); Sandor Farkas, Budapest (HU); György Domany, Budapest (HU); Istvan Borza, Budapest (HU); Gizella Bartane Szalai, Budapest (HU); Jozsef Nagy, Budapest (HU); Sandor Kolok, Budapest (HU)

(73) Assignee: Richter Gedeon Vegyeszeti Gyar Rt., Budapest (HU)

( * ) Notice: Subject to any disclaimer, the term of this patent is extended or adjusted under 35 U.S.C. 154(b) by 492 days.

(21) Appl. No.: 11/024,638

(22) Filed: Dec. 28, 2004

(65) Prior Publication Data

US 2005/0113360 A1 May 26, 2005

Related U.S. Application Data

(60) Division of application No. 10/412,977, filed on Apr. 11, 2003, now Pat. No. 6,919,355, which is a continuation-in-part of application No. PCT/HU01/00099, filed on Oct. 15, 2001.

(30) Foreign Application Priority Data

Oct. 24, 2000 (HU) ................................. P0004123

(51) Int. Cl.
*A61K 31/445* (2006.01)
*C07D 401/06* (2006.01)
(52) U.S. Cl. ........................ 514/322; 546/199; 548/218
(58) Field of Classification Search ................ 514/322; 546/199, 218
See application file for complete search history.

(56) References Cited

U.S. PATENT DOCUMENTS 5,866,589 A * 2/1999 Romero et al. ............. 514/318
6,476,041 B1 11/2002 Thompson et al. ..... 514/263.22

FOREIGN PATENT DOCUMENTS

| EP | 0 105 763 | 4/1984 |
| WO | WO 96/18628 | 11/1995 |
| WO | WO 98/14427 | 8/1997 |
| WO | WO 00/00197 | 6/1999 |
| WO | WO 00/12074 | 8/1999 |
| WO | WO 00/42213 | 1/2000 |

OTHER PUBLICATIONS

Sobol et al. "Preclinical evaluation . . . " Neuropharmacology v.51, p. 933-946 (2006).*
Borza et al. "Indole-2-carboxamines . . . " Bioorg. Med. Chem. v.13, p. 3859-3861 (2003).*
Borza et al. "Selective NR1/2B . . . " J. Med. Chem. v.50 p. 901-014 (2007).*

Johnson, M.I., Bunge, R.P. (1992), 51-75, Primary cell cultures of peripheral and central neurons and glia.
Helva. Chim. Acta., 51, 1616 (1968).
Helva. Chim. Acta., 77, 100 (1994).
J. Chem. Soc. 1605-1608 (1948).
Tetrahedron 54, 13981 (1998).
Helva. Chim. Acta., 135 (1949).
Bioorganic & Medicinal Chemistry Letters 10 (2000) 483-486; Karen Milkiewicz et al; The design, synthesis and activity . . . .
Protein Science (1997) 6:1412-1417; Nickolay Chirgadze et al; The crystal structure of human a-thrombin . . . .
J. Med. Chem. 1996, 39, 3769-3789; Donna Romero et al; Targeting delavirdine/atevirdine resistant HIV-1: . . . .
J. Med. Chem. 1999, 42, 4140-4149; Michael Genin et al; Synthesis and structure—activity relationships . . . .
XP-002191279 Chem. Abstracts (Indian J. Chem 1970).
XP-002191278 Chem. Abstract Svce Columbus Ohio (Acta Pol. Pharm 1974).
"Synthesis and biological evaluation of novel piperiodine . . . " by Lubisch et al. (Biorg. & Med. Chem. Letters Oct. 2000.

(Continued)

*Primary Examiner*—Celia Chang
(74) *Attorney, Agent, or Firm*—Jonathan Myers; Andrew Wilford

(57) ABSTRACT

Compounds having NR2B selective NMDA receptor antagonist activity are disclosed of the formula (I)

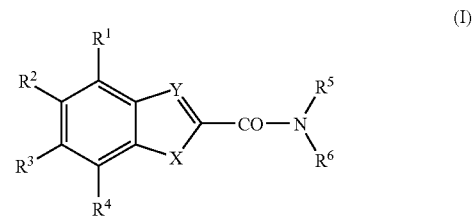

(I)

wherein
  two of the neighboring $R^1$, $R^2$, $R^3$ and $R^4$ groups form an oxo-oxazolidine ring fused to the benzene ring of the indole nucleus,
  and the other two of $R^1$, $R^2$, $R^3$ and $R^4$ groups are hydrogen atoms,
  $R^5$ and $R^6$ together with the nitrogen between them form a saturated or unsaturated, 4-6 membered heterocyclic ring, which is substituted by phenoxy, phenyl-($C_1$-$C_4$ alkyl), phenyl-($C_1$-$C_4$ alkoxy), phenoxy-($C_1$-$C_4$ alkyl), or benzoyl, optionally substituted on the aromatic ring by one or more halogen atoms, cyano or hydroxy groups, $C_1$-$C_4$ alkyl or $C_1$-$C_4$ alkoxy groups,
  X is NH—,
  Y is a —CH— group,
  or pharmaceutically acceptable salts thereof formed with acids or bases.

10 Claims, No Drawings

OTHER PUBLICATIONS

"The reduction of aromatic nitro groups . . . " by Scheuermann et al (Tetrahedron Letters 41/2000).
Ennis et al "Preparation of dioxino[2,3-e]indole . . . " CA 115:279812 (1991).
Font et al "Indoles and pyridazino[4,5-b]indoles . . . " CA 124:164316 (1996).
Berger et al "Preparation of substituted aromatic . . . " CA 135:92639 (2001).
Andersson et al "Preparation of heterocyclic pharmaceutical . . . " CA 2001:816656 (2001).
Pabel et al "Synthesis and resolution of racemic eliprodil . . . " Bioorganic & Med. Chem. Letters 10 (2000) 1377-1380.
J. Med. Chem. 1978, vol. 21, No. 3, pp. 309-312; Piperidylalkylindoles. 1. Hypotensive activity . . . .
J. Med. Chem. 1992, 35, pp. 4903-4910; Ketanserin analogues: structure-affinity relationships for . . . .
TINS, vol. 10, No. 7, 1987, pp. 299-302; Excitotoxicity and the NMDA receptor.
Curr. Pharm. Des. 1999, 5, pp. 381-404; Antagonists selective for NMDA receptors containing . . . .
Stroke, 28, 1997, pp. 2244-2251; Effect of CP101,606, a novel NR2B subunit antagonist . . . .
Brain Res. 792, 1998, pp. 291-298; Effects of the NMDA antagonist CP-98,113 on regional . . . .
Exp. Neurol. 163, 2000, pp. 239-243; Antiparkinsonian actions of CP-101,606, an antagonist . . . .
Neuropharmacology 38, 1999, pp. 611-623; Selective NMDA NR2B antagonists Induce . . . .
Drug News Perspect 11, 1998, pp. 523-569; Glutamate in CNS disorders as a target for . . . .
Eur. J. Neuroscience, vol. 10, 1998, pp. 1704-1715; Developmental changes in localization . . . .
Meth. Cell. Biol. 40, 1994, pp. 155-181; Practical aspects of measuring . . . .
J. Chem. Soc., 321, 1938, pp. 321-329; The unsaturation and tautomeric . . . .
J. Am. Chem. Soc., 80, 1958, pp. 1657-1662; Synthesis of some substituted . . . .
J. Org. Chem., 64, 1999, pp. 3763-3766; A practical synthesis of . . . .
J. Med. Chem., 18, 926 (1975).

* cited by examiner

AMIDE DERIVATIVES AS NMDA RECEPTOR ANTAGONISTS

CROSS REFERENCE TO RELATED APPLICATION

This application is a divisional of Ser. No. 10/412,977 filed 11 Apr. 2003 now U.S. Pat. No. 6,919,355 which is a continuation-in-part of International Application PCT/HU01/00099, with an international filing date of 15 Oct. 2001, published in English under PCT Article 21(2) and now abandoned, and which claims the priority of Hungarian Patent Application P00 04123 filed 24 Oct. 2000.

FIELD OF THE INVENTION

The invention relates to new NMDA receptor antagonist carboxylic acid amide derivatives of formula (I)

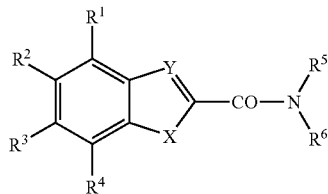

(I)

wherein
one of the neighboring $R^1$, $R^2$, $R^3$ and $R^4$ groups is OH or NH2 and the others are each hydrogen, or
two of the neighboring $R^1$, $R^2$, $R^3$ and $R^4$ groups in given case together with one or more identical or different additional hetero atom and —CH= and/or —CH$_2$— groups form a 5-6 membered homo- or heterocyclic ring, preferably pyrrole, pyrazole, imidazole, oxazole, oxo-oxazolidine, or 3-oxo-1,4-oxazine ring, and the other two of $R^1$, $R^2$, $R^3$ and $R^4$ groups are hydrogen atoms,
$R^5$ and $R^6$ together with the nitrogen between them form a saturated or unsaturated, 4-6 membered heterocyclic ring, which is substituted by hydroxy group, and/or in given case phenyl or phenoxy, phenyl-($C_1$-$C_4$ alkyl), phenyl-($C_1$-$C_4$ alkoxy), phenoxy-($C_1$-$C_4$ alkyl), anilino, phenyl-($C_1$-$C_4$ alkylamino), [phenyl-($C_1$-$C_4$ alkyl)]-amino, benzoyl, hydroxy-diphenylmethyl, $C_1$-$C_4$ alkoxycarbonyl-phenoxymethyl or benzhydrylidene group, optionally substituted on the aromatic ring by one or more halogen atom, cyano or hydroxy group, $C_1$-$C_4$ alkyl or $C_1$-$C_4$ alkoxy group,
X is independently oxygen, —NH— or a CH2 group,
Y is independently a nitrogen atom or a —CH— group,
and the salts thereof formed with acids and bases.

As the invention relates also to the salts of compounds of formula (I) formed with acids or bases, especially the salts formed with pharmaceutically acceptable acids or bases, the meaning of compound of formula (I) is either the free compound or the salt even if it is not referred separately.

An especially significant group of the invention is the compounds of formula (Ia),

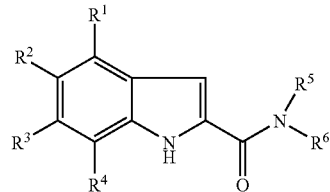

(Ia)

wherein the meaning of $R^1$, $R^2$, $R^3$, $R^4$, $R^5$ and $R^6$ is as described for the compounds of formula (I).

Especially important carboxylic acid amide derivatives of formula (I) are the following:
6-(4-benzylpiperidine-1-carbonyl)]-1,5-dihydro-oxazolo[4,5-f]indole-2-one,
6-[4-(4-fluorobenzylpiperidine-1-carbonyl)]-1,5-dihydro-oxazolo[4,5-f]indole-2-one,
(4-benzylpiperidine-1-yl)-(3,6-dihydro-pyrrolo[3,2-e]indazol-7-yl)methanone,
[4-(4-fluorobenzylpiperidine-1-yl)]-(3,6-dihydro-pyrrolo[3,2-e]indazol-7-yl)methanone,
(4-p-tolyloxypiperidine-1-yl)]-(3,6-dihydro-pyrrolo[3,2-e]indazol-7-yl)methanone,
(4-benzylpiperidine-1-yl)-(3,6-dihydro-imidazo[4,5-e]indol-7-yl)methanone.

The invention also relates to the pharmaceutical compositions containing the compounds of formula (I) as active ingredient.

Furthermore objects of the present invention are the synthesis of compounds of formula (I), and the chemical and pharmaceutical manufacture of medicaments containing these compounds, as well as the method of treatments with these compounds, which means administering to a mammal to be treated—including human—effective amount/amounts of compounds of formula (I) of the present invention as such or as medicament.

The term "halogen" substituent—as defined earlier—denotes fluorine, chlorine, bromine or iodine atoms, preferably fluorine and chlorine atoms. The term $C_1$-$C_4$ alkyl group used in the present description denotes methyl, ethyl, normal- and isopropyl and different butyl groups. These $C_1$-$C_4$ alkyl groups can be in the $C_1$-$C_4$ alkoxy groups. The term $C_1$-$C_6$ alkanoyloxy group denotes a monovalent acyloxy group consisting of a hydrogen atom, as well as a $C_1$-$C_6$ alkyl group and a carbonyl-oxy group (—CO—O—) attached to it, preferably a formyloxy, an acetoxy, a propionyloxy, different butiryloxy, valeroyloxy and caproyloxy groups.

The invention relates also to the salts of compounds of formula (I) formed with acids or bases.

Both organic and inorganic acids can be used for the formation of acid addition salts. Suitable inorganic acids can be for example hydrochloric acid, sulfuric acid and phosphoric acid. Representatives of monovalent organic acids can be for example formic acid, acetic acid, propionic acid, and different butyric acids, valeric acids and capric acids. Representatives of bivalent organic acids can be for example oxalic acid, malonic acid, maleic acid, fumaric acid and succinic acid. Other organic acids can also be used, such as hydroxy acids for example citric acid, tartaric acid, or aromatic carboxylic acids for example benzoic acid or salicylic acid, as well as aliphatic and aromatic sulfonic acids for example methanesulfonic acid and p-toluenesulfonic acid. Especially valuable group of the acid addition salts is in which the acid component itself does not have therapeutical effect in the applied dose or it does not have unfavorable influence on the effect of the active ingredient. These acid addition salts are pharmaceutically acceptable acid addition salts. The reason why acid addition salts, which do not belong to the pharmaceutically acceptable acid addition salts belong to the present invention is, that in given case they can be advantageous in the purification and isolation of the desired compounds.

Among the salts formed with bases especially important are the salts formed with alkali metals, for example sodium, potassium, alkaline-earth metals, for example calcium and magnesium, as well as with ammonia or organic amines. The latter bases can have further substituents, for example hydroxy or amino groups, which can influence e.g. the solubility and the handling of the product.

According to the invention the compounds of formula (I) are synthesized by forming an amide bond between a carboxylic acid of formula (II)

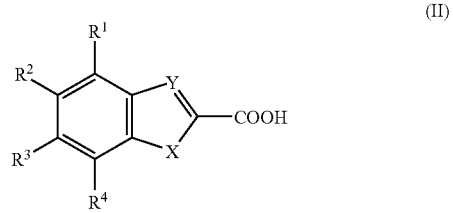

(II)

wherein the meaning of $R^1$, $R^2$, $R^3$, $R^4$, X and Y are as described before for the formula of (I)—and an amine of formula (III)

(III)

wherein the meaning of $R^5$ and $R^6$ are as given before for the formula of (I), then the so obtained carboxylic acid amide derivative of formula (I)—wherein the meaning of $R^1$, $R^2$, $R^3$, $R^4$, $R^5$, $R^6$, X and Y is as defined for the formula of (I)—in given case is transformed into an other compound of formula (I) by introducing new substituents and/or modifying or removing the existing ones, and/or salt formation and/or liberating the compound from salts, and/or the obtained racemates are resolved using optical active acids or bases by known methods.

The amide bond formation is preferably carried out by preparing an active derivative from a carboxylic acid of formula (II) and this is reacted with an amine of formula (III) preferably in the presence of a base.

In solution the transformation of a carboxylic acid into an active derivative is carried out in situ during the amide bond formation in a proper solvent (for example dimethylformamide, acetonitrile, chlorinated hydrocarbons or hydrocarbons). The active derivatives can be acid chlorides (for example prepared from carboxylic acid with thionyl chloride), mixed anhydrides (for example prepared from carboxylic acid with isobutyl chloroformate in the presence of a base, e.g. triethylamine), active esters (for example prepared from carboxylic acid with hydroxybenztriazol and dicyclohexyl-carbodiimide or O-benzotriazol-1-yl-N,N,N',N'-tetramethyluronium hexafluorophosphate (HBTU) in the presence of a base e.g. triethylamine). The active derivatives are prepared between room temperature and 0° C. To the so obtained solution or suspension a proper amine of formula (III) is added as base or as a salt formed with inorganic acid so that base, for example triethylamine, needed for the liberation of the amine is added to the reaction mixture separately. The condensation reactions are followed by thin layer chromatography. The necessary reaction time is 6-20 h. The work-up of the reaction mixture can be carried out by different methods.

When the reaction mixture is a suspension, the precipitate is filtered off and recrystallized from a proper solvent to give the pure product. If the crystallization does not lead to the pure product, then column chromatography can be used for the purification of it. The column chromatography is carried out either on normal phase using Kieselgel 60 as adsorbent and different solvent systems, e.g. toluene/methanol, chloroform/methanol or toluene/acetone, as eluents, or on reverse phase using Prep-Pak-500/C18 type packings (produced by Waters Associates) and acetonitrile/water/trifluoroacetic acid as eluent. If the reaction mixture is a solution at the end of the acylation, it is concentrated, and the residue is crystallized or purified by column chromatography as described above. The structures of the products are determined by IR, NMR and mass spectrometry.

Alternatively, the reaction mixture can be purified by column chromatography without concentration at the end of the reaction. The fractions having the desired compound are concentrated, the residue is dissolved in dimethylsulfoxide and the structure, the purity as well as the concentration of the product is determined by HPLC/MS (high pressure column chromatography, followed by mass spectrometry).

The obtained carboxylic acid amide derivatives of formula (I) independently from the method of preparation—in given case can be transformed into an other compound of formula (I) by introducing further substituents and/or modifying and/or removing the existing ones, and/or formation of salts with acids and/or liberating the carboxylic acid amide derivative of formula (I) from the obtained acid addition salts by treatment with a base and/or the free carboxylic acid amide derivative of formula (I) can be transformed into a salt by treatment with a base.

The carboxylic acids of formula (II) and the amines of formula (III) are either commercially available or can be synthesized by different known methods. The syntheses of some commercially not available carboxylic acid of formula (II) are described in the Examples. Following these procedures the other commercially not available carboxylic acids of formula (II) can also be prepared.

The compounds of the invention as well as their pharmaceutically acceptable salts can be used as such or suitably in the form of pharmaceutical compositions. These compositions (drugs) can be in solid, liquid or semiliquid form and pharmaceutical adjuvant and auxiliary materials can be added, which are commonly used in practice, such as carriers, excipients, diluents, stabilizers wetting or emulsifying agents, pH- and osmotic pressure-influencing, flavoring or aromatizing, as well as formulation-promoting or formulation-providing additives.

The dosage required to exert the therapeutical effect can vary within wide limits and will be fitted to the individual requirements in each of the particular case, depending on the stage of the disease, the condition and the bodyweight of the patient to be treated, as well as the sensitivity of the patient against the active ingredient, route of administration and number of daily treatments. The actual dose of the active ingredient to be used can safely be determined by the attending physician skilled in the art in the knowledge of the patient to be treated.

The pharmaceutical compositions containing the active ingredient according to the present invention usually contain 0.01 to 100 mg of active ingredient in a single dosage unit. It is, of course possible that the amount of the active ingredient in some compositions exceeds the upper or lower limits defined above.

The solid forms of the pharmaceutical compositions can be for example tablets, dragées, capsules, pills or lyophilized powder ampoules useful for the preparation of injections. Liquid compositions are the injectable and infusable compositions, fluid medicines, packing fluids and drops. Semi-liquid compositions can be ointments, balsams, creams, shaking mixtures and suppositories.

For the sake of a simple administration it is suitable if the pharmaceutical compositions comprise dosage units containing the amount of the active ingredient to be administered once, or a few multiples or a half, third or fourth part thereof. Such dosage units are e.g. tablets, which can be powdered with grooves promoting the halving or quartering of the tablet in order to exactly administer the required amount of the active ingredient.

Tablets can be coated with an acid-soluble layer in order to assure the release of the active ingredient content after leaving the stomach. Such tablets are enteric-coated. A similar effect can be achieved also by encapsulating the active ingredient.

The pharmaceutical compositions for oral administration can contain e.g. lactose or starch as excipients, sodium carboxymethylcellulose, methylcellulose, polyvinyl pyrrolidine or starch paste as binders or granulating agents. Potato starch or microcrystalline cellulose is added as disintegration agents, but ultraamylopectin or formaldehyde casein can also be used. Talcum, colloidic silicic acid, stearin, calcium or magnesium stearate can be used as antiadhesive and lubricants.

The tablet can be manufactured for example by wet granulation, followed by pressing. The mixed active ingredients and excipients, as well as in given case part of the disintegrants are granulated with an aqueous, alcoholic or aqueous alcoholic solution of the binders in an appropriate equipment, then the granulate is dried. The other disintegrants, lubricants and antiadhesive agents are added to the dried granulate, and the mixture is pressed to a tablet. In given case the tablets are made with halving groove to ease the administration.

The tablets can be made directly from the mixture of the active ingredient and the proper auxiliaries by pressing. In given case, the tablets can be coated by using additives commonly used in the pharmaceutical practice, for example stabilizers, flavoring, coloring agents, such as sugar, cellulose derivatives (methyl- or ethylcellulose, sodium carboxymethylcellulose, etc), polyvinyl pyrrolidone, calcium phosphate, calcium carbonate, food coloring agents, food laces, aroma agents, iron oxide pigments, etc. In the case of capsules the mixture of the active ingredient and the auxiliaries is filled into capsules.

Liquid oral compositions, for example suspensions, syrups, elixirs can be made by using water, glycols, oils, alcohols, coloring and flavoring agents.

For rectal administration the composition is formulated in suppositories or clysters. The suppository can contain beside the active ingredient a carrier, so called adeps pro suppository. Carriers can be vegetable oils, such as hydrogenated vegetable oils, triglycerides of $C_{12}$-$C_{18}$ fatty acids (preferably the carriers under the trade name Witepsol). The active ingredient is homogeneously mixed with the melted adeps pro suppository and the suppositories are moulded.

For parenteral administration the composition is formulated as injection solution. For manufacturing the injection solution the active ingredients are dissolved in distilled water and/or in different organic solvents, such as glycolethers, in given case in the presence of solubilizers, for example polyoxyethylensorbitane-monolaurate, -monooleate, or monostearate (Tween 20, Tween 60, Tween 80). The injection solution can also contain different auxiliaries, such as conserving agents, for example ethylendiamine tetraacetate, as well as pH adjusting agents and buffers and in given case local anaesthetic, e.g. lidocain. The injection solution containing the active ingredient of the invention is filtered before it is filled into ampoules, and it is sterilized after filling.

If the active ingredient is hygroscopic, then it can be stabilized by liophylization.

Close structure analogs of the carboxylic acid amide derivatives of formula (I) are known from the literature.

Substituted indole-2-yl-carbonyl-piperidine derivatives, similar to the compounds of the invention, are described in patent No. WO 9618628 and two publications [J. Med. Chem., 39, 3769. (1996), and J. Med. Chem., 42, 4140. (1999)]. These compounds having reverse transcriptase inhibiting effect can be used for treatment of AIDS patients.

Indole-2-carboxylic acid amides are also known [Bioorg. Med. Chem. Letters, 10, 483. (2000)] to inhibit pp60$^{c-arc}$ tyrosine kinase, and therefor they can play a role in treatment of tumor patients. The publication does not describe NMDA receptor antagonist effect.

Benzofuran-2-yl-piperidine derivatives are described in patent No. WO 2000012074. These compounds have p38-a kinase inhibiting effect, and therefor can be used for treatment of infections caused by gram-negative bacteria as well as of patients suffering from respiratory distress syndrome.

A methanone derivative described in Protein Sci., 6(7), 1412. (1997) have thrombin inhibiting effect. The publication does not describe NMDA receptor antagonist effect.

Surprisingly it was found, that in contrast to the known, structurally analog compounds—which are known to have only different enzyme inhibiting effects—the new carboxylic acid amide derivatives of formula (I) of the present invention are highly effective and selective antagonists of NMDA (N-methyl-D-aspartate) receptors, and moreover most of the compounds are selective antagonist of NR2B subtype of NMDA receptor. This selectivity is particularly important, as the undesired side effects of the compounds are less pronounced.

Antagonists of the NMDA receptors can be used in many disorders that are accompanied with excess release of glutamate, the main excitatory neurotransmitter in the central nervous system. Overactivation of NMDA receptors by glutamate can lead to calcium overload of the cells. This can trigger cascade of intracellular events that can alter the cell function and can lead even to death of neurons [TINS, 10, 299-302 (1987)].

Our knowledge of NMDA receptor structure, function and pharmacology has expanded owing to recent achievements of molecular biology. The NMDA receptors are heteromeric assemblies built up from at least one NR1 subunit and at least one of the four NR2 subunits (NR2A-D). Both spatial distributions in CNS and pharmacological sensitivity of NMDA receptors built up from various NR2 subunits are different. Particularly interesting of these is NR2B subunit, because of its restricted distribution (highest density is in forebrain and substantia gelatinosa of spinal cord). Compounds selective for this subtype are available [Curr. Pharm. Des. 5, 381-404 (1999)] and were proven to be effective in animal models of stroke [Stroke 28, 2244-2251 (1997)], traumatic brain injury [Brain Res. 792, 291-298 (1998)], Parkinson's disease [Exp. Neurol. 163 239-243 (2000)], neuropathic and inflammatory pain [Neuropharmacology 38, 611-623 (1999)]. Subtype selective antagonists of NMDA receptors are expected to exhibit little or no untoward side effects caused by non-selective antagonists of NMDA receptors acting at glutamate binding site or within the channel pore.

Disorders known to be responsible to NMDA antagonists [Drug News Perspect 11, 523-569 (1998), WO 00/00197 international patent application] are cerebral ischemia of any origin (e.g. stroke, heart surgery), chronic neurodegenerative disorders, such as Alzheimer's disease, Parkinson's disease, amyotrophic lateral sclerosis (ALS), Huntington's disease, human immunodeficiency virus (HIV) related neuronal injury, traumatic injury of brain or spinal cord, pain (e.g. posttraumatic or postoperative) and chronic pain states, such as neuropathic pain or cancer related pain. NMDA receptor antagonists may also be used in epilepsy, anxiety, depression, migraine, psychosis, muscular spasm, multiinfarct dementia and in dementia of other origin, hypoglycemia, degenerative disorders of the retina (e.g. CMV retinitis) asthma, tinnitus, aminoglycoside antibiotic-induced hearing loss. An NMDA antagonist can be useful to decrease tolerance and/or dependence to opioid treatment of pain, and for treatment of withdrawal syndrome of e.g. alcohol, opioids, and cocaine.

As the target compounds have the above mentioned biological effects, objects of the present invention are also the process of treatments with carboxylic acid amide derivatives of formula (I), or with the salts thereof, which means administering to a mammal to be treated—including human—effective amount/amounts of compounds of formula (I) of the present invention as such or as medicament.

It is known that during postnatal development the subunit composition of neuronal NMDA receptors is changing. Similar change was detected in neuronal cell cultures [Eur. J. Neurosci. 10, 1706-1715 (1998)]. According to literature data and to our own immunocitochemical examinations neuronal cells cultured for 6-7 days in vitro predominantly express the NR2B subunit, together with NR1 subunit. So functional test of NMDA antagonism in these cells mostly reflects action on NR2B subunit containing receptors. Since NMDA receptors are known to be permeable to calcium ions upon excitation, we characterized the NMDA receptor activation by measurement of rise in intracellular calcium concentration following the agonist (NMDA) application to the cells.

Assessment of NMDA Antagonist Potency In Vitro by Measurement of Intracellular Calcium Concentration with a Plate Reader Fluorimeter The intracellular calcium measurements were carried out on primary neocortical cell cultures derived from 17 day old Charles River rat embryos (for the details on the preparation of neocortical cell culture see Johnson, M. I.; Bunge, R. P. (1992): Primary cell cultures of peripheral and central neurons and glia. In: Protocols for Neural Cell Culture, eds: Fedoroff, S.; Richardson A., The Humana Press Inc., 13-38.) After isolation the cells were plated onto standard 96-well microplates and the cultures were maintained in an atmosphere of 95% air-5% $CO_2$ at 37° C. until the calcium measurements.

The cultures were used for the intracellular calcium measurements after 4-7 days in vitro. Before the measurement the cells were loaded with a fluorescent $Ca^{2+}$-sensitive dye, Fluo-4/AM (2-2.5 µM). To stop the loading the cells were washed twice with the solution used for the measurement (140 mM NaCl, 5 mM KCl, 2 mM $CaCl_2$, 5 mM HEPES, 5 mM HEPES-Na, 20 mM glucose, 10 µM glycine, pH=7.4). After washing the test compounds were added to the cells in the above solution (90 µl/well). Intracellular calcium measurements were carried out with a plate reader fluorimeter: elevation of Fluo-4-fluorescence and so, intracellular calcium was induced by application of 40 µM NMDA. Inhibitory potency of the test compounds was assessed by measuring the reduction in the calcium elevation in the presence of different concentrations of the compounds. After the measurement a standard calibration procedure with slight modifications was used to convert the fluorescent data to calcium concentration values [Meth. Cell. Biol. 40, 155-181 (1994)].

Dose-response curves and $IC_{50}$-values were calculated by using data derived from at least three independent experiments. Inhibitory potency of a compound at a single concentration point was expressed as percent inhibition of the NMDA response. Sigmoidal concentration-inhibition curves were fit to the data and $IC_{50}$ values were determined as the concentration that produces half of the maximal inhibition caused by the compound.

In Table 1 $IC_{50}$ values for the most effective compounds of this invention measured in this test are listed (column 1-2) together with most effective reference compounds examined (column 3-4).

TABLE 1

| Code number of compound | NMDA $IC_{50}$ [µM] | Code of reference compound | NMDA $IC_{50}$ [µM] |
|---|---|---|---|
| 4570001461 | 0.017 | Co-101244 | 0.023 |
| 4570001689 | 0.020 | EMD 95885 | 0.035 |
| 4570001690 | 0.022 | CP 101,606 | 0.041 |
| 4570001484 | 0.041 | Co-111103 | 0.060 |
| 4570002260 | 0.042 | Ro 25.6981 | 0.159 |
| 4570001779 | 0.050 | ifenprodil | 0.483 |
| 4570001662 | 0.058 | | |
| 4570001462 | 0.079 | | |
| 4570001688 | 0.088 | | |
| 4570002340 | 0.127 | | |
| 4570001661 | 0.150 | | |
| 4570001972 | 0.193 | | |
| 4570001971 | 0.328 | | |
| 4514305 | 0.392 | | |
| 4570002045 | 0.44 | | |
| 4513579 | 0.018 | | |
| 4513848 | 0.09 | | |
| 4570001103 | 0.0022 | | |
| 4570001378 | 0.009 | | |

The reference compounds are as follows:

Co 101244: 1-[2-(4-hydroxyphenoxy)ethyl]-4-hydroxy-4-(4-methylbenzyl)piperidine

EMD 95885: 6-[3-(4-fluorobenzyl)piperidine-1-yl]propionyl]-2,3-dihydro-benzoxazol-2-on CP-101,606: (1S,2S)-1-(4-hydroxyphenyl)-2-(4-hydroxy-4-phenylpiperidine-1-yl)-1-propanol Co-111103: 1-[2-(4-hydroxyphenoxy) ethyl]-4-(4-fluorobenzyl)piperidine Ro 256981: R-(R*,S*)-1-(4-hydroxyphenyl)-2-methyl-3-[4-(phenylmethyl)piperidin-1-yl]-1-propanol.

As Table 1 shows, many of the compounds of this invention exceeds the potency of the known reference compounds examined by us.

Testing Subunit Selectivity on Cells Expressing Recombinant Rat NMDA Receptors

In order to prove NR2B subunit selectivity of the compounds, cells transfected with cDNAs of the rat NR1a and NR2A or NR2B subunits were used. Genes cloned according to published sequences [gi508809 (rat NR1a), gi205738 (rat NR2B), gi2905805 (rat NR2A)] were inserted into inducible mammalian expression vectors bearing different resistance genes (hygromycine in case of NR1a or neomycine in case of NR2 subunits). The vector constructs were introduced into HEK293 cells using a cationic lipid-mediated transfection method. Protein expression was induced by 3 μM MuristeronA. Cells were maintained in the presence of 365 μM ketamine for 48-72 hours under an atmosphere of 95% air-5% $CO_2$ at 37° C. before the experiments.

Assessment of NMDA Antagonist Potency on Cells Transfected with NR1a/NR2B Subunits—Fluorimetric Method For establishment of cell clones stably expressing NR1a/NR2B receptors, transfected cells were exposed to the selecting antibiotics for 4 weeks then resistant clones were grown up. The expression of NR2B subunit protein was verified by a flow cytometry based immunocytochemical method. Positive clones were further tested for functional activity in patch clamp experiments. The best clone producing the highest NMDA evoked ion-current was used for testing NMDA antagonism by measuring NMDA induced elevation of cytosolic calcium concentration. Induction of protein expression and maintenance of cells were the same as described above.

The cells were plated onto standard 96-well microplates. A plate reader-based fluorometric assay was used to measure NMDA antagonism. The method was essentially similar to that described above for testing primary cultures of rat cortical neurons.

Assessment of NMDA Antagonist Potency on Cells Transfected with NR1a/NR2A Subunits—Patch Clamp Method Cells transiently expressing NR1a/NR2A receptors and grown onto coverslips were used in patch clamp experiments. Whole-cell patch clamp recording was done according to the standard technique. Cell cultures were constantly superfused with an extracellular solution (140 mM NaCl, 5 mM KCl, 5 mM Hepes, 5 mM Na-Hepes, 2 mM $CaCl_2$, 20 mM glucose, 10 μM glycine, pH 7.35) at room temperature. Patch pipettes with resistance between 3 and 6 MΩ were filled with an intracellular solution (140 mM CsCl, 11 mM EGTA, and 10 mM Hepes, pH 7.3). The inward current elicited by 100 μM NMDA was recorded from cells voltage clamped at −70 mV. Compounds were applied via a multi-barrel ejection device controlled by electromagnetic valves. First NMDA was repeatedly administered until stabilization of responses, then it was given in the presence of the test compound. The degree of inhibition—expressed as percentage—was calculated from the peak currents evoked by NMDA in the presence and absence of the test compound. Selectivity ratio (NR2B/NR2A), was calculated as the ratio of test dose on NR1/2A transfected cells and $IC_{50}$ value of NMDA antagonism on NR1/NR2B expressing cells.

The results are given in Table 2.

TABLE 2

Assessment of selectivity for NR2B vs. NR2A subunit containing receptors

| Compound | NR1/NR2B* $IC_{50}$ [μM] | NR1/NR2A** % Inhibition of NMDA $Ca^{2+}$-response 15 μM | Selectivity |
|---|---|---|---|
| 4570001461 | 0.015 | 14.9 | >1000 |
| 4570002260 | 0.030 | 3.3 | >500 |
| CP-101,606 | 0.033 | −8.8 | >1200 |

*Data obtained on HEK293 cells stably expressing NR1a/NR2B subunits by measurement of intracellular calcium concentration with a plate reader fluorimeter. Means of 3 experiments are given.
**results of patch clamp experiments on NR1a/NR2A transiently transfected HEK cells.
Test concentration was as indicated. Means of 3, 6, 2 experiments are given for 4570001461, 4570002260 and CP-101,606 respectively.

Selectivity: selectivity ratio (NR2B/NR2A), calculated as ratio of test concentration on NR1/NR2A transfected cells and $IC_{50}$ value on NR1/NR2B expressing cells.

According to the results in Table 2, compounds 4570001461 and 4570002260 as well as CP-101,606 are highly selective toward NR2B subunit containing NMDA receptors.

The synthesis of compounds and pharmaceutical compositions according to the invention is illustrated by the following not limiting Examples. The code numbers of the compounds, which are referred in the biological tests, are given after the name of the compounds prepared in the Examples.

EXAMPLE 1

6-(4-Benzylpiperidin-1-carbonyl)-3H-furo[3',2':4,5]benzo[1,2-d]oxazole-2-one (45 14255)

a) Ethyl 3H-furo[2,3-f]benzoxazole-2-one-6-carboxylate

A mixture of 0.9 g (4.2 mmol) of ethyl 5-hydroxy-6-aminobenzofuran-2-carboxylate [Helv. Chim. Acta 77, 100. (1994)], 60 ml of tetrahydrofuran, 3.1 ml of 20% phosgene in toluene solution and 2.0 ml of triethylamine is stirred at room temperature for 1 h. The tetrahydrofuran is distilled off in vacuum, water is added to the residue and the product is extracted with ethyl acetate. The combined organic layers are washed with 5% aqueous sodium hydrogencarbonate solution, water, 1 N hydrochloric acid solution and again with water, dried over sodium sulfate and concentrated to yield 1.0 g (96%) of the title compound as oil.

b) 3H-Furo[2,3-f]benzoxazole-2-one-6-carboxylic Acid

A stirred mixture of 1.0 g (4 mmol) of ethyl 3H-furo[2,3-f]benzoxazole-2-one-6-carboxylate, 100 ml of ethanol and 0.5 g of potassium hydroxide is refluxed for 1 h. The mixture is concentrated, the residue is dissolved in water and acidified with 20% aqueous sulfuric acid solution. The precipitated crystals are filtered off and washed with water to yield 0.84 g (95%) of the title compound. Mp.: 190-192° C. (water).

c) 6-(4-Benzylpiperidin-1-carbonyl)-3H-furo[3',2':4, 5]benzo[1,2-d]oxazole-2-one A mixture of 0.42 g (1.9 mmol) of 3H-furo[2,3-f]benzoxazole-2-one-6-carboxylic acid, 0.3 ml (2.1 mmol) of triethylamine, 0.35 ml (2.0 mmol) of 4-benzylpiperidine, 0.76 g (2.0 mmol) of HBTU (Advanced Chem. Tech.) and 10 ml of dimethylformamide is stirred at room temperature for 6 h. The reaction mixture is concentrated and the residue is purified by column chromatography using Kieselgel 60 as adsorbent (Merck) and toluene:aceton=2:1 as eluent, then the product is crystallized with diethylether to yield 0.39 g (54%) of the title compound. Mp.: 205-210° C. (diethyl ether).

EXAMPLE 2

6-(4-Benzyloxypiperidin-1-carbonyl)-3H-furo[3',2': 4,5]benzo[1,2-d]oxazole-2-one (45 14254)

The title compound is prepared from 3H-furo[2,3-f]benzoxazole-2-one-6-carboxylic acid and 4-benzyloxypiperidine according to the method described in Example 1/c. Mp.: 217-219° C. (diethyl ether).

EXAMPLE 3

1-(4-Benzylpiperidin-1-yl)-1-(1,6-dihydro-1,6-diaza-as-indacene-2-yl)methanone (45 14305)

a) Methyl (Z)-2-azido-3-(1H-indole-5-yl)acrylate

Under nitrogen, to a sodium methoxide solution (prepared from 15 ml of methanol and 0.66 g (29 mmol) of sodium) a mixture of 1.02 g (7 mmol) of indole-5-carbaldehyde [Helv. Chim. Acta, 1616. (1968)], 3.34 g (29 mmol) of methyl azido-acetate and 7 ml of methanol is added dropwise at 0° C. and the so obtained mixture is stirred at this temperature for 5 h. Then the reaction mixture is diluted with 50 ml of water, and extracted three times with 50 ml of chloroform. The combined organic layers are washed with 20 ml of water, filtered through a phase separating filterpaper and concentrated to yield 1.3 g (77%) of the title compound. Mp.: 130-133° C. (chloroform).

b) Methyl 1,6-dihydro-1,6-diaza-as-indacene-2-carboxylate

To a boiling solution of 36 ml of xylene 1.09 g (4.5 mmol) of methyl (Z)-2-azido-3-(1H-indole-5-yl)acrylate is added in small portions. The reaction mixture is refluxed till the end of the nitrogen gas formation, then concentrated and the residue is crystallized with hexane, the product is filtered and washed with hexane to yield 0.6 g (62%) of the title compound. Mp.: 183-184° C. (hexane).

c) 1,6-Dihydro-1,6-diaza-as-indacene-2-carboxylic acid

A mixture of 0.53 g (2.5 mmol) of methyl 1,6-dihydro-1,6-diaza-as-indacene-2-carboxylate, 0.36 g (2.5 mmol) of potassium trimethylsilanolate (Aldrich) and 6.0 ml of tetrahydrofuran is refluxed for 1 h, further 0.18 g (1.25 mmol) of potassium trimethylsilanolate is added and after 5 h reflux the reaction mixture is concentrated. The residue is mixed with 20 ml of water, the undissolved material is filtered off, 0.32 ml of hydrochloric acid is added to the filtrate, the precipitated crude product is filtered off and purified by column chromatography using Kieselgel 60 (Merck) as adsorbent, and chloroform:methanol=9:1 as eluent. The product is crystallized with diethyl ether to yield 0.22 g (44%) of the title compound. Mp.: 248-250° C. (diethyl ether).

d) 1-(4-Benzylpiperidin-1-yl)-1-(1,6-dihydro-1,6-diaza-as-indacene-2-yl)methanone The title compound is prepared from 1,6-dihydro-1,6-diaza-as-indacene-2-carboxylic acid and 4-benzylpiperidine according to the method described in Example 1/c. Mp.: 186-188° C. (diethyl ether).

EXAMPLE 4

(4-Benzylpiperidin-1-yl)-(2-propyl-8H-oxazolo[5,4-g]indol-7-yl)methanone (4570001079)

a) 1-(4-Benzylpiperidine-1-yl)-1-(6-hydroxy-1H-indole-2-yl)methanone

A mixture of 5.0 g (28.2 mmol) of 6-hydroxy-indole-2-carboxylic acid [J. Chem. Soc. 1605-1608. (1948)], 4.4 ml (31.6 mmol) of triethylamine, 5.0 g (28.5 mmol) of 4-benzylpiperidine, 12.0 g (31.6 mmol) of HBTU (Advanced Chem. Tech.) and 50 ml of dimethylformamide is stirred at room temperature for 6 h. The precipitated product is filtered off and recrystallized from ethanol to yield 6.75 g (71%) of the title compound. Mp: 214-215° C. (ethanol).

b) (4-Benzylpiperidin-1-yl)-(2-propyl-8H-oxazolo[5, 4-g]indol-7-yl)methanone

Under argon, to a solution of 0.5 g (1.49 mmol) of 1-(4-benzylpiperidine-1-yl)-1-(6-hydroxy-1H-indole-2-yl) methanone and 0.14 g (0.2 mmol) of n-butylamine in 100 ml of ethylene glycol dimethyl ether 10 g (115 mmol) of manganese dioxide is added portion-wise at 0° C. After stirring for 1 h, the reaction mixture is filtered, the filtrate is concentrated and the residue is purified by column chromatography using Kieselgel 60 as adsorbent (Merck) and hexane:ethyl acetate=2:1 as eluent to yield 0.1 g (17.3%) of the title compound. Mp.: 195-196° C. (hexane-ethyl acetate).

EXAMPLE 5

6-(4-Benzylpiperidin-1-carbonyl)-1,5-dihydro-oxazolo[4,5-f]indole-2-one (4570001461)

a) Methyl (Z)-2-azido-3-(4-benzyloxy-3-nitrophenyl)acrylate

Under argon, to a sodium methoxide solution (prepared from 2.5 g (108.7 mmol) of sodium and 70 ml of methanol) a mixture of 6.1 g (23.7 mmol) of 4-benzyloxy-3-nitrobenzaldehyde and 11.2 g (97.3 mmol) of methyl azidoacetate in 100 ml of methanol is added at 0° C. The mixture is stirred at 0° C. for 5 h, then diluted with 350 ml of water, the precipitated crystals were filtered off, washed with water and dried to yield 4.93 g (59%) of the title compound. Mp.: 95-96° C. (water).

b) Methyl 6-benzyloxy-5-nitro-indole-2-carboxylate

To a stirred solution of 200 ml of boiling xylene 4.93 g ((13.9 mmol) of methyl (Z)-2-azido-3-(4-benzyloxy-3-nitrophenyl)acrylate is added in small portions. After completion of the addition the reaction mixture is refluxed until the gas formation is over (about 0.5 h), then cooled to room temperature, the precipitated product is filtered off and washed with n-hexane to yield 0.67 g (15%) of the title compound. Mp.: 184-187° C. (xylene).

c) Methyl 5-amino-6-hydroxy-indole-2-carboxylate

A mixture of 0.67 g (2.0 mmol) of methyl 6-benzyloxy-5-nitro-indole-2-carboxylate, 60 ml of tetrahydrofuran and 0.1 g of 10% Pd/C catalyst is hydogenated for 5 h. The catalyst is filtered off and the filtrate containing the title compound is used immediately in the next step.

d) Methyl 2-oxo-1,5-dihydro-2H-oxazolo[4,5-f]indole-6-carboxylate

The title compound is prepared from methyl 5-amino-6-hydroxy-indole-2-carboxylate according to the method described in Example 1/a. Mp.: 267-277° C. (water).

e) 2-Oxo-1,5-dihydro-2H-oxazolo[4,5-f]indole-6-carboxylic Acid

The title compound is prepared from methyl 2-oxo-1,5-dihydro-2H-oxazolo[4,5-f]indole-6-carboxylate according to the method described in Example 1/b. Mp.: 288-290° C. (water).

f) 6-(4-Benzylpiperidin-1-carbonyl)-1,5-dihydro-oxazolo[4,5-f]indole-2-one

The title compound is prepared from 2-oxo-1,5-dihydro-2H-oxazolo[4,5-f]indole-6-carboxylic acid and 4-benzylpiperidine according to the method described in Example 1/c. Mp.: 270-271° C. (diethyl ether).

EXAMPLE 6

6-(4-Benzyloxypiperidin-1-carbonyl)-1,5-dihydro-oxazolo[4,5-f]indole-2-one (4570001462)

The title compound is prepared from 2-oxo-1,5-dihydro-2H-oxazolo[4,5-f]indole-6-carboxylic acid and 4-benzyloxypiperidine [Tetrahedron 54, 13981, (1998)] according to the method described in Example 1/c. Mp.: 258-261° C. (diethyl ether).

EXAMPLE 7

6-[4-(4-Fluorobenzyl)piperidin-1-carbonyl]-1,5-dihydro-oxazolo[4,5-f]indole-2-one (4570001484)

The title compound is prepared from 2-oxo-1,5-dihydro-2H-oxazolo[4,5-f]indole-6-carboxylic acid and 4-(4-fluorobenzyl)piperidine [J. Med. Chem., 35, 4903, (1992)] according to the method described in Example 1/c. Mp.: 244-247° C. (diethyl ether).

EXAMPLE 8

[4-(4-Fluorobenzyl)piperidin-1-yl]-(1,6-dihydro-pirrolo[2,3-g]indazol-7-yl)-methanone (the Other Tautomeric Form of the Compound is [4-(4-fluorobenzyl)piperidin-1-yl]-(3,6-dihydro-pirrolo[2,3-g]indazol-7-yl)-methanone) (4570001661)

a) Ethyl 2-[(1H-indazol-6-yl)-hydrazono]-propionate (the Other Tautomeric Form of the Compound is Ethyl 2-[(3H-indazol-6-yl)-hydrazono]-propionate)

To a stirred mixture of 6.66 g (50 mmol) of 6-aminoindazole, 40 ml of water and 25 ml of concentrated hydrochloric acid a solution of 3.5 g sodium nitrite in 10 ml of water is added dropwise at 0° C., and stirring is continued at this temperature for 0.5 h. Then the so obtained solution is added to the following stirred mixture: 86 ml of water, 15 g of potassium hydroxide, 15 g of sodium acetate, 60 ml of ethanol and 8 ml of ethyl 2-methyl-acetoacetate (purity 90%). After the addition the reaction mixture is stirred at 0° C. for 1 h, the precipitated product is filtered off, washed with water and dried to yield 8.16 g (66%) of the title compound. Mp.: 210-211° C. (ethanol).

b) Ethyl 1,6-dihydro-pyrrolo[2,3-g]indazole-7-carboxylate (the Other Tautomeric Form of the Compound is Ethyl 3,6-dihydro-pyrrolo[2,3-g]indazole-7-carboxylate)

A mixture of 4.0 g (16.2 mmol) of ethyl 2-[(1H-indazol-6-yl)-hydrazono]-propionate and 20 g of polyphosphoric acid is slowly warmed to 120° C. and kept at this temperature for 0.5 h. Then the reaction mixture is cooled to room temperature, 30 ml of water and 15 ml of concentrated hydrochloric acid is added. The so obtained mixture is extracted with ethyl acetate, dried over sodium sulfate and concentrated to yield 1.6 g (43%) of the title compound. Mp.: 120-121° C. (ethyl acetate).

c) 1,6-Dihydro-pyrrolo[2,3-g]indazole-7-carboxylic Acid (the Other Tautomeric Form of the Compound is 3,6-dihydro-pyrrolo[2,3-g]indazole-7-carboxylic Acid)

The title compound is prepared from ethyl 1,6-dihydro-pyrrolo[2,3-g]indazole-7-carboxylate according to the method described in Example 1/b. Mp.: 270-275° C. (water).

d) [4-(4-Fluorobenzyl)piperidin-1-yl]-(1,6-dihydro-pirrolo[2,3-g]indazol-7-yl)-methanone (the Other Tautomeric Form of the Compound is [4-(4-fluorobenzyl)piperidin-1-yl]-(3,6-dihydro-pirrolo[2,3-g]indazol-7-yl)-methanone)

The title compound is prepared from 1,6-dihydro-pyrrolo[2,3-g]indazole-7-carboxylic acid and 4-(4-fluorobenzyl)piperidine according to the method described in Example 1/c. Mp.: 162-165° C. (diethyl ether).

EXAMPLE 9

(4-Benzylpiperidin-1-yl)-(1,6-dihydro-pirrolo[2,3-g] indazol-7-yl)-methanone (the Other Tautomeric Form of the Compound is (4-benzylpiperidin-1-yl)-(3,6-dihydro-pirrolo[2,3-g]indazol-7-yl)-methanone) (4570001662)

The title compound is prepared from 1,6-dihydro-pyrrolo[2,3-g]indazole-7-carboxylic acid and 4-benzylpiperidine according to the method described in Example 1/c. Mp.: 209-210° C. (diethyl ether).

EXAMPLE 10

[4-(4-Fluorobenzyl)piperidin-1-yl]-(3,6-dihydro-imidazo[4,5-e]indol-7-yl)methanone (the Other Tautomeric Form of the Compound is [4-(4-fluorobenzyl)piperidin-1-yl]-(1,6-dihydro-imidazo[4,5-e]indol-7-yl)methanone) (4570001688)

a) Ethyl 2-[(1H-benzimidazol-5-yl)-hydrazono]-propionate (the Other Tautomeric Form of the Compound is Ethyl 2-[(3H-benzimidazol-5-yl)-hydrazono]-propionate)

The title compound is prepared from 5-amino-benzimidazole [Helv. Chim. Acta, 32, 135 (1949)] according to the method described in Example 8/a. Mp.: 121-127° C. (water).

b) Ethyl 3,6-dihydro-imidazo[4,5-e]indole-7-carboxylate (the Other Tautomeric Form of the Compound is Ethyl 1,6-dihydro-imidazo[4,5-e]indole-7-carboxylate)

The title compound is prepared from ethyl 2-[(1H-benzimidazol-5-yl)-hydrazono]-propionate according to the method described in Example 8/b. Mp.: foam.

c) 3,6-Dihydro-imidazo[4,5-e]indole-7-carboxylic Acid (the Other Tautomeric Form of the Compound is 1,6-dihydro-imidazo[4,5-e]indole-7-carboxylic Acid)

The title compound is prepared from ethyl 3,6-dihydro-imidazo[4,5-e]indole-7-carboxylate according to the method described in Example 1/b. Mp.: 185-190° C. (water).

d) [4-(4-Fluorobenzyl)piperidin-1-yl]-(3,6-dihydro-imidazo[4,5-e]indol-7-yl)methanone (the Other Tautomeric Form of the Compound is [4-(4-fluorobenzyl)piperidin-1-yl]-(1,6-dihydro-imidazo[4,5-e]indol-7-yl)methanone The title compound is prepared from 3,6-dihydro-imidazo[4,5-e]indole-7-carboxylic acid and 4-(4-fluorobenzyl)piperidine according to the method described in Example 1/c. Mp.: 283-287° C. (diethyl ether).

EXAMPLE 11

(4-Benzylpiperidin-1-yl)-(3,6-dihydro-pirrolo[3,2-e]indazol-7-yl)methanone (the Other Tautomeric Form of the Compound is (4-benzylpiperidin-1-yl)-(1,6-dihydro-pirrolo[3,2-e]indazol-7-yl)methanone) (4570001689)

a) Ethyl 2-[(1H-indazol-5-yl)-hydrazono]-propionate (the Other Tautomeric Form of the Compound is Ethyl 2-[(3H-indazol-5-yl)-hydrazono]-propionate)

The title compound is prepared from 5-aminoindazole according to the method described in Example 8/a. Mp.: 111-113° C. (water).

b) Ethyl 3,6-dihydro-pyrrolo[3,2-e]indazole-7-carboxylate (the Other Tautomeric Form of the Compound is Ethyl 1,6-dihydro-pyrrolo[3,2-e]indazole-7-carboxylate)

The title compound is prepared from ethyl 2-[(1H-indazol-5-yl)-hydrazono]-propionate according to the method described in Example 8/b. Mp.: 220-221° C. (methanol).

c) 3,6-Dihydro-pyrrolo[3,2-e]indazole-7-carboxylic Acid (the Other Tautomeric Form of the Compound is 1,6-dihydro-pyrrolo[3,2-e]indazole-7-carboxylic Acid)

The title compound is prepared from ethyl 3,6-dihydro-pyrrolo[3,2-e]indazole-7-carboxylate according to the method described in Example 1/b. Mp.: 183-189° C. (water).

d) (4-Benzylpiperidin-1-yl)-(3,6-dihydro-pirrolo[3,2-e]indazol-7-yl)methanone (the Other Tautomeric Form of the Compound is (4-benzylpiperidin-1-yl)-(1,6-dihydro-pirrolo[3,2-e]indazol-7-yl)methanone)

The title compound is prepared from 3,6-dihydro-pyrrolo[3,2-e]indazole-7-carboxylic acid and 4-benzylpiperidine according to the method described in Example 1/c. Mp.: 205-207° C. (diethyl ether).

EXAMPLE 12

[4-(4-Fluorobenzyl)piperidin-1-yl]-(3,6-dihydro-pirrolo[3,2-e]indazol-7-yl)methanone (the Other Tautomeric Form of the Compound is [4-(4-fluorobenzyl)piperidin-1-yl]-(1,6-dihydro-pirrolo[3,2-e]indazol-7-yl)methanone) (4570001690)

The title compound is prepared from 3,6-dihydro-pyrrolo[3,2-e]indazole-7-carboxylic acid and 4-(4-fluorobenzyl)piperidine according to the method described in Example 1/c. Mp.: 169-173° C. (diethyl ether).

EXAMPLE 13

(4-Benzylpiperidin-1-yl)-(3,6-dihydro-imidazo[4,5-e]indol-7-yl)methanone (the Other Tautomeric Form of the Compound is (4-benzylpiperidin-1-yl)-(1,6-dihydro-imidazo[4,5-e]indol-7-yl)methanone) (4570001779)

The title compound is prepared from 3,6-dihydro-imidazo[4,5-e]indole-7-carboxylic acid and 4-benzylpiperidine according to the method described in Example 1/c. Mp.: 256-257° C. (diethyl ether).

EXAMPLE 14

7-(4-Benzylpiperidin-1-carbonyl)-1,6-dihydro-3-oxa-1,6,8-triaza-as-indacen-2-one (the Other Tautomeric Form of the Compound is 7-(4-benzylpiperidin-1-carbonyl)-1,8-dihydro-3-oxa-1,6,8-triaza-as-indacen-2-one) (4570001971)

a) N-Butyl-N'-(4-methoxy-2-nitrophenyl)-oxalamide

To a suspension of 44.0 g (164 mmol) of N-(4-methoxy-2-nitrophenyl)-oxalamic acid ethyl ester [J. Med. Chem., 18, 926 (1975)] in 330 ml of toluene 16.8 ml (170 mmol) of n-butylamine is added dropwise keeping the temperature below 20° C., then the mixture is stirred at room temperature overnight. The reaction mixture is concentrated and 200 ml of diethyl ether is added to the residue. The so obtained suspension is filtered, washed with diethyl ether and dried to yield 45.3 g (93%) of the title compound. Mp.: 127-128° C. (diethyl ether).

b) N-(2-Amino-4-methoxyphenyl)-N'-butyl-oxalamide

A mixture of 27.0 g (91 mmol) of N-butyl-N'-(4-methoxy-2-nitrophenyl)-oxalamide, 1200 ml of methanol and 7.3 g of 10% Pd/C catalyst is hydogenated for 3 h. The catalyst is filtered off, washed with aceton, the filtrate is concentrated and the residue is treated with 100 ml of diethyl ether. The obtained product is filtered, washed with diethyl ether a nd dried to yield 21.8 g (90%) of the title compound. Mp.: 180-181° C. (diethyl ether).

c) 6-Methoxy-1H-benzimidazole-2-carboxylic Acid Butylamide (the Other Tautomeric Form of the Compound is 5-methoxy-1H-benzimidazole-2-carboxylic Acid Butylamide)

Under nitrogen, 41.0 g (154 mmol) of N-(2-amino-4-methoxyphenyl)-N'-butyl-oxalamide is heated to 240° C. for 10 min. After cooling the residue is treated with 300 ml of aceton, filtered and the filtrate is concentrated. The so obtained residue is crystallized with 150 ml of hexane, filtered and dried to yield 26.5 g (69.5%) of the title compound. Mp.: 125-126° C. (hexane).

d) 6-Hydroxy-1H-benzimidazole-2-carboxylic Acid (the Other Tautomeric Form of the Compound is 5-hydroxy-1H-benzimidazole-2-carboxylic Acid)

A solution of 26.0 g (105 mmol) of 6-methoxy-1H-benzimidazole-2-carboxylic acid butylamide in 780 ml of 48% hydrogen bromide is stirred at 90° C. for 12 h, then at 125° C. for 12 h. The reaction mixture is cooled, the precipitated product is filtered off, washed with water and dried to yield 14.4 g (76%) of the title compound. Mp.: 206-207° C. (water).

e) 6-Hydroxy-7-nitro-1H-benzimidazole-2-carboxylic Acid (the Other Tautomeric Form of the Compound is 5-hydroxy-4-nitro-1H-benzimidazole-2-carboxylic Acid)

To a solution of 2.0 g (11.2 mmol) of 6-hydroxy-1H-benzimidazole-2-carboxylic acid in 25 ml of trifluoroacetic acid 1.0 g (11.7 mmol) of sodium nitrate is added below 20° C. and the mixture is stirred at 20° C. for 2 h. The reaction mixture is poured into ice-water, the precipitated product is filtered off, washed with water and dried to yield 1.7 g (68%) of the title compound. Mp.: 218° C. (water).

f) (4-Benzylpiperidin-1-yl)-(6-hydroxy-7-nitro-1H-benzimidazol-2-yl)methanone (the Other Tautomeric Form of the Compound is (4-benzylpiperidin-1-yl)-(5-hydroxy-4-nitro-1H-benzimidazol-2-yl) methanone)

The title compound is prepared from 6-hydroxy-7-nitro-1H-benzimidazole-2-carboxylic acid and 4-benzylpiperidine according to the method described in Example 1/c. Mp.: 102° C. (diethyl ether).

g) (7-Amino-6-hydroxy-1H-benzimidazol-2-yl)-(4-benzylpiperidin-1-yl)methanone (the Other Tautomeric Form of the Compound is (4-amino-5-hydroxy-1H-benzimidazol-2-yl)-(4-benzylpiperidin-1-yl)methanone A mixture of 1.0 g of (4-benzylpiperidin-1-yl)-(6-hydroxy-7-nitro-1H-benzimidazol-2-yl)methanone, 30 ml of methanol and 0.4 g of 10% Pd/C catalyst is hydogenated for 2 h. The catalyst is filtered off and the filtrate is concentrated. The residue is treated with diethyl ether, the crystalline product is filtered, washed with diethyl ether and dried to yield 0.5 g (54%) of the title compound. Mp.: 108° C. (diethyl ether).

h) 7-(4-Benzylpiperidin-1-carbonyl)-1,6-dihydro-3-oxa-1,6,8-triaza-as-indacen-2-one (the Other Tautomeric Form of the Compound is 7-(4-benzylpiperidin-1-carbonyl)-1,8-dihydro-3-oxa-1,6,8-triaza-as-indacen-2-one)

To a solution of 0.45 g (1.28 mmol) of (7-amino-6-hydroxy-1H-benzimidazol-2-yl)-(4-benzylpiperidin-1-yl) methanone in 5 ml of tetrahydrofuran 0.2 g (1.37 mmol) of 1,1'-carbonyldiimidazole is added at 20° C. The reaction mixture is stirred at room temperature for 2 h, then concentrated. The residue is purified by column chromatography using Kieselgel 60 as adsorbent (Merck) and toluene:methanol=4:1 as eluent. The so obtained product is crystallized with isopropanol, filtered and dried to yield 0.45 g (93.5%) of the title compound. Mp.: >270° C. (isopropanol).

EXAMPLE 15

6-(4-Benzylpiperidin-1-carbonyl)-3,5-dihydro-imidazo[4',5';4,5]benzo[1,2-d]oxazole-2-one (the Other Tautomeric Form of the Compound is 6-(4-benzylpiperidin-1-carbonyl)-3,7-dihydro-imidazo[4',5'; 4,5]benzo[1,2-d]oxazole-2-one) (4570001972)

a) 6-Amino-5-nitro-3H-benzoxazol-2-one

To a solution of 2.0 g (13.3 mmol) of 6-amino-3H-benzoxazol-2-one [J. Chem. Soc., 321 (1938)] in 20 ml of trifluoroacetic acid 1.2 g (14.1 mmol) of sodium nitrate is added below 20° C. The reaction mixture is stirred at room temperature overnight, then concentrated. The residue is purified by column chromatography using Kieselgel 60 as adsorbent (Merck) and toluene:methanol=4:1 as eluent to yield 2.50 g (96%) of the title compound. Mp.: 198° C. (toluene-methanol).

b) (4-Benzylpiperidin-1-yl)oxoacetic Acid Ethyl Ester

To a solution of 10 g (57 mmol) of 4-benzylpiperidine and 10 ml (57.4 mmol) of N-ethyldiisopropylamine in 100 ml of dichloromethane 7.05 ml (63.1 mmol) of ethyl oxalyl chloride is added dropwise at 0° C., then the mixture is stirred at this temperature for 30 min. The reaction mixture is diluted with water, separated, the organic layer is dried and concentrated to yield 15.5 g (99%) of the title compound as an oil.

c) (4-Benzylpiperidin-1-yl) oxoacetic Acid

A mixture of 15.5 g (56 mmol) of (4-benzylpiperidin-1-yl)oxoacetic acid ethyl ester, 5 g (79.4 mmol) of potassium hydroxide and 250 ml of methanol is stirred at room temperature for 6 h. Then reaction mixture is concentrated, the residue is taken up in water, acidified with 1N hydrochloric acid, the precipitated product is filtered off, washed with water and dried to yield 11.95 g (85%) of the title compound. Mp.: 115° C. (water).

d) (4-Benzylpiperidin-1-yl)oxoacetyl Chloride

A mixture of 26.2 g (106 mmol) of (4-benzylpiperidin-1-yl)oxoacetic acid and 50 ml of thinyl chloride is refluxed for 2 h, then cooled and concentrated to yield 28.0 g (99.5%) of the title compound as an oil.

e) 2-(4-Benzylpiperidin-1-yl)-N-(5-nitro-2-oxo-2,3-dihydro-benzoxazol-6-yl)-2-oxo-acetamide To a solution of 3.23 g (16.56 mmol) of 6-amino-5-nitro-3H-benzoxazole-2-one (step a), 2.58 ml (18.5 mmol) of trethylamine and 100 ml of chloroform 5.25 g (19.75 mmol) of (4-benzylpiperidin-1-yl)oxoacetyl chloride in 20 ml of chloroform is added dropwise at 20° C., then the mixture is stirred at room temperature for 2 h. The mixture is washed with water, the organic layer is dried and concentrated. The residue is purified by column chromatography using Kieselgel 60 as adsorbent (Merck) and toluene:methanol=4:1 as eluent to yield 3.3 g (47%) of the title compound. Mp.: foam.

f) N-(5-Amino-2-oxo-2,3-dihydro-benzoxazol-6-yl)-2-(4-benzylpiperidin-1-yl)-2-oxo-acetamide A mixture of 3.3 g (7.7 mmol) of 2-(4-benzylpiperidin-1-yl)-N-(5-nitro-2-oxo-2,3-dihydro-benzoxazol-6-yl)-2-oxo-acetamide, 100 ml of methanol and 0.3 g of 10% Pd/C catalyst is hydrogenated for 8 h. The catalyst is filtered off and the filtrate is concentrated. The residue is purified by column chromatography using Kieselgel 60 as adsorbent (Merck) and toluene:acetone=2:1 as eluent to yield 1.06 g (34.5%) of the title compound. Mp.: 296° C. (toluene-acetone).

g) 6-(4-Benzylpiperidin-1-carbonyl)-3,5-dihydro-imidazo[4',5';4,5]benzo[1,2-d]oxazole-2-one (the Other Tautomeric Form of the Compound is 6-(4-benzylpiperidin-1-carbonyl)-3,7-dihydro-imidazo[4',5';4,5]benzo[1,2-d]oxazole-2-one)

1.0 g (2.5 mmol) of N-(5-amino-2-oxo-2,3-dihydro-benzoxazol-6-yl)-2-(4-benzylpiperidin-1-yl)-2-oxo-acetamide is heated to 240° C. for 10 min, then cooled. The obtained mixture is purified by column chromatography using Kieselgel 60 as adsorbent (Merck) and toluene:acetone=1:1 as eluent to yield 0.16 g (17%) of the title compound. Mp.: >290° C. (toluene-acetone).

EXAMPLE 16

6-(4-Benzylpiperidin-1-carbonyl)-3,5-dihydro-1H-imidazo[4,5-f]indole-2-one (4570002045)

a) Ethyl 2-[(2-oxo-2,3-dihydro-1H-benzimidazol-5-yl)-hydrazono]-propionate

The title compound is prepared from 5-amino-1,3-dihydro-benzimidazol-2-one [J. Am. Chem. Soc., 80, 1657 (1958)] according to the method described in Example 8/a. Mp.: 220° C. (water).

b) Ethyl 2-oxo-1,2,3,5-tetrahydro-imidazo[4,5-f]indole-6-carboxylate

The title compound is prepared from ethyl 2-[(2-oxo-2,3-dihydro-1H-benzimidazol-5-yl)-hydrazono]-propionate according to the method described in Example 8/b. Mp.: 196-197° C. (ethyl acetate).

c) 2-Oxo-1,2,3,5-tetrahydro-imidazo[4,5-f]indole-6-carboxylic Acid

The title compound is prepared from ethyl 2-oxo-1,2,3,5-tetrahydro-imidazo[4,5-f]indole-6-carboxylate according to the method described in Example 1/b. Mp.: >270° C. (water).

d) 6-(4-Benzylpiperidin-1-carbonyl)-3,5-dihydro-1H-imidazo[4,5-f]indole-2-one The title compound is prepared from 2-oxo-1,2,3,5-tetrahydro-imidazo[4,5-f]indole-6-carboxylic acid and 4-benzylpiperidine according to the method described in Example 1/c. Mp.: >270° C. (acetonitrile).

EXAMPLE 17

2-(4-Benzylpiperidin-1-carbonyl)-1,5-dihydro-8-oxa-1,5-diaza-cyclopenta[b]naphthalene-6-one (4570002185)

a) Methyl 6-oxo-1,5,6,7-tetrahydro-8-oxa-1,5-diaza-cyclopenta[b]naphthalene-2-carboxylate To a solution of 2.0 g (9.7 mmol) of methyl 5-amino-6-hydroxy-indole-2-carboxylate (Example 5/c) in 300 ml of tetrahydrofuran 2.45 g (29.2 mmol) of sodium hydrogencarbonate and 1.3 ml (16.3 mmol) of chloroacetyl chloride are added and the mixture is stirred at room temperature overnight. The reaction mixture is concentrated and 100 ml of water is added to the residue. The precipitated crystals are filtered off, washed with water and suspended in 120 ml of acetonitrile. 4.05 g (29.3 mmol) of potassium carbonate is added to the suspension and the resulted mixture is stirred at room temperature overnight. The reaction mixture is concentrated and 100 ml of water is added to the residue. The product is filtered off, washed with water and dried to yield 1.7 g (71%) of the title compound. Mp.: 188-196° C. (water).

b) 6-Oxo-1,5,6,7-tetrahydro-8-oxa-1,5-diaza-cyclopenta[b]naphthalene-2-carboxylic Acid The title compound is prepared from methyl 6-oxo-1,5,6,7-tetrahydro-8-oxa-1,5-diaza-cyclopenta[b]naphthalene-2-carboxylate according to the method described in Example 8/b. Mp.: 231-237° C. (water).

c) 2-(4-Benzylpiperidin-1-carbonyl)-1,5-dihydro-8-oxa-1,5-diaza-cyclopenta[b]naphthalene-6-one The title compound is prepared from 6-oxo-1,5,6,7-tetrahydro-8-oxa-1,5-diaza-cyclopenta[b]naphthalene-2-carboxylic acid and 4-benzylpiperidine according to the method described in Example 1/c. Mp.: 225-231° C. (diethyl ether).

EXAMPLE 18

2-[4-(4-Fluorobenzyl)piperidin-1-carbonyl]-1,5-dihydro-8-oxa-1,5-diaza-cyclopenta[b]naphthalene-6-one (4570002193)

The title compound is prepared from 6-oxo-1,5,6,7-tetrahydro-8-oxa-1,5-diaza-cyclopenta[b]naphthalene-2-carboxylic acid and 4-(4-fluorobenzyl)piperidine according to the method described in Example 1/c. Mp.: 219-226° C. (diethyl ether).

EXAMPLE 19

(3,6-Dihydro-pirrolo[3,2-e]indazol-7-yl)-(4-p-tolyloxypiperidin-1-yl)methanone (the Other Tautomeric Form of the Compound is (1,6-dihydro-pirrolo[3,2-e]indazol-7-yl)-(4-p-tolyloxypiperidin-1-yl)methanone) (4570002260)

The title compound is prepared from 3,6-dihydro-pyrrolo[3,2-e]indazole-7-carboxylic acid (Example 11/c) and 4-p-tolyloxypiperidine [J. Med. Chem., 21, 309 (1978)] according to the method described in Example 1/c. Mp.: 218-222° C. (diethyl ether).

EXAMPLE 20

(3,6-Dihydro-pirrolo[3,2-e]indazol-7-yl)-[4-(4-methylbenzyl)piperidin-1-yl]methanone (the Other Tautomeric Form of the Compound is (1,6-dihydro-pirrolo[3,2-e]indazol-7-yl)-[4-(4-methylbenzyl)piperidin-1-yl]methanone) (4570002340)

The title compound is prepared from 3,6-dihydro-pyrrolo[3,2-e]indazole-7-carboxylic acid (Example 11/c) and 4-(4-methylbenzyl)piperidine [J. Org. Chem., 64, 3763 (1999)] according to the method described in Example 1/c. Mp.: 253-255° C. (diethyl ether).

EXAMPLE 21

1-(4-Benzylpiperidine-1-yl)-1-(6-hydroxy-1H-indole-2-yl)methanone (45 13579)

A mixture of 5.0 g (28.2 mmol) of 6-hydroxy-indole-2-carboxylic acid [J. Chem. Soc. 1605-1608. (1948)], 4.4 ml (31.6 mmol) of triethylamine, 5.0 g (28.5 mmol) of 4-benzylpiperidine, 12.0 g (31.6 mmol) of HBTU (Advanced Chem. Tech.) and 50 ml of dimethylformamide is stirred at room temperature for 6 h. The precipitated product is filtered off and recrystallized from ethanol to yield 6.75 g (71%) of the title compound. Mp: 214-215° C. (ethanol).

EXAMPLE 22

1-[4-(4-Fluorobenzyl)piperidine-1-yl]-1-(6-hydroxy-1H-indole-2-yl)methanone (45 13848)

The title compound is prepared from 4-(4-fluorobenzyl)piperidine [J. Med. Chem., 35, 4903. (1992)] and 6-hydroxy-1H-indole-2-carboxylic acid in acetonitrile at room temperature. The reaction mixture is concentrated and the residue is purified by column chromatography using Kiesel gel 60 as adsorbent (Merck) and toluene:methanol=4:1 as eluent. Mp.: 180-182° C. (toluene).

EXAMPLE 23

1-(4-Benzylpiperidine-1-yl)-1-(5-nitro-1H-indole-2-yl)methanone (45 14205)

The title compound is prepared from 5-nitroindole-2-carboxylic acid (J. Am. Chem. Soc., 4621 (1958)] and 4-benzylpiperidine according to the method described in Example 1/c. Mp.: 220-224° C. (diethylether).

EXAMPLE 24

1-(5-Amino-1H-indole-2-yl)-1-(4-benzylpiperidine-1-yl)methanone (45 14244)

A mixture of 0.5 g (1.38 mmol) of 1-(4-benzylpiperidine-1-yl)-1-(5-nitro-1H-indole-2-yl)methanone, 20 ml of methanol and 0.1 g of 10% Pd/C catalyst is hydrogenated for 5 h. The catalyst is filtered off, washed with methanol and the filtrate is concentrated. The residue is treated with diethylether and the precipitated crystals are filtered off to yield 0.27 g (59%) of the title compound. Mp.: 175-180° C. (diethylether).

EXAMPLE 25

(4-Benzylpiperidine-1-yl)-(6-hydroxy-1H-benzoimidazol-2-yl) methanone (45 70001103)

a) N-Butyl-N'-(4-methoxy-2-nitro-phenyl)oxalamide

To a suspension of 44.0 g (164 mmol) of N-(4-methoxy-2-nitro-phenyl)oxalamic acid ethyl ester [J. Med. Chem., 18, 926 (1975)] and 330 ml toluene 16.8 ml (170 mmol) of n-butylamin is added under 20° C. The reaction mixture is stirred at room temperature for 10 h, then concentrated and the residue is crystallized with diethyl ether, the precipitated product is filtered off, washed with diethyl ether and dried to yield 45.3 g (93.3%) of the title compound. Mp.: 127-128° C. (diethyl ether).

b) N-(2-Amino-4-methoxy-phenyl)-N'-butyl-oxalamide

A mixture of 27.0 g (91 mmol) of N-Butyl-N'-(4-methoxy-2-nitro-phenyl) oxalamide, 1200 ml of methanol and 7.3 g of 5% Pd/C catalyst is hydrogenated from 3 h. To the reaction mixture is added 600 ml of acetone. The catalyst is filtered off, washed with acetone, the filtrate is concentrated and the residue si crystallized with diethyl ether to yield 21.8 g (90.1%) of the titled compound. Mp.: 180-181° C. (diethyl ether).

c) 6-Methoxy-1H-benzoimidazole-2-carboxylic Acid Butylamide

Under nitrogen, 41.0 g (154 mmol) of N-(2-amino-4-methoxy-phenyl)-N'-butil-oxalamide is stirred at 240° C. for 10 min. The mixture is cooled to room temperature then 300 ml of acetone is added, and stirred for 1 h. The precipitated product is filtered off. The filtrate is concentrated and the residue is mixed with 150 ml of n-hexane. The precipitated product is filtered off, washed with hexane and dried to yield 26.5 g (69.5%) of the title compound. Mp.: 125-126° C. (n-hexane).

d) 6-Hydroxy-1H-benzoimidazole-2-carboxylic Acid

A mixture of 26.0 g (105 mmol) of 6-methoxy-1H-benzoimidazole-2-carboxylic acid butilamide and 780 ml of 48% aqueus hydrobromic acid is stirred at 110° C. for 8 h, then refluxed for 12 h. The mixture is cooled to room temperature, the precipitated product is filtered off, washed with water until pH neutral and dried to yield 14.3 g (76.2%) of the title compound. Mp.: 206-207° C. (water).

e) (4-Benzylpiperidine-1-yl)-(6-hydroxy-1H-benzoimidazol-2-yl)-methanone (45 70001103)

A mixture of 3.0 g (16.75 mmol) of 6-hydroxi-1H-benzoimidazol-2-carboxilic acid, 2.4 ml (17.2 mmol) of triethylamin, 3.0 g (17.1 mmol) of 4-benzyl-piperidine, 7.0 g (18.5 mmol) of HBTU and 100 ml of dimethylformamide is stirred at room temperature for 16 h. The reaction mixture is concentrated and the residue is purified by column chromatography using Kieselgel 60 as adsorbent (Merck) and toluene:methanol=4:1 as eluent, then the product is recrystallized from toluene to yield 3.58 g (63.5%) of the title compound. Mp.: 186° C. (toluene).

EXAMPLE 26

(6-Hydroxy-1H-benzoimidazol-2-yl)-[4-(4-methyl-benzyl)-piperidine-1-yl]-methanone 45 70001378

The title compound is prepared from 6-hydroxy-1H-benzoimidazole-2-carboxylic acid [Example elözö d] and 4-(-methylbenzyl)piperidine [J. Org. Chem., 64, 3763 (1999)] according to the method described in Example 25. Mp.: 93° C. (diisopropyl ether).

EXAMPLE 27

Preparation of Pharmaceutical Compositions:

a) Tablets:
0.01-50% of active ingredient, 15-50% of lactose, 15-50% of potato starch, 5-15% of polyvinyl pyrrolidone, 1-5% of talc, 0.01-3% of magnesium stearate, 1-3% of colloid silicon dioxide and 2-7% of ultraamylopectin are mixed, then are granulated by wet granulation and pressed to tablets.

b) Dragées, Filmcoated Tablets:
The tablets made according to the method described above are coated by a layer consisting of entero- or gastro-solvent film, or of sugar and talc. The dragées are polished by a mixture of beeswax and carnuba wax.

c) Capsules:
0.01-50% of active ingredient, 1-5% of sodium lauryl sulfate, 15-50% of starch, 15-50% of lactose, 1-3% of colloid silicon dioxide and 0.01-3% of magnesium stearate are thoroughly mixed, the mixture is passed through a sieve and filled in hard gelatin capsules.

d) Suspensions:
Ingredients: 0.01-15% of active ingredient, 0.1-2% of sodium hydroxide, 0.1-3% of citric acid, 0.05-0.2% of nipagin (sodium methyl 4-hydroxybenzoate), 0.005-0.02% of nipasol, 0.01-0.5% of carbopol (polyacrilic acid), 0.1-5% of 96% ethanol, 0.1-1% of flavoring agent, 20-70% of sorbitol (70% aqueous solution) and 30-50% of distilled water.

To solution of nipagin and citric acid in 20 ml of distilled water, carbopol is added in small portions under vigorous stirring, and the solution is left to stand for 10-12 h. Then the sodium hydroxide in 1 ml of distilled water, the aqueous solution of sorbitol and finally the ethanolic raspberry flavor are added with stirring. To this carrier the active ingredient is added in small portions and suspended with an immersing homogenizator. Finally the suspension is filled up to the desired final volume with distilled water and the suspension syrup is passed through a colloid milling equipment.

e) Suppositories:
For each suppository 0.01-15% of active ingredient and 1-20% of lactose are thoroughly mixed, then 50-95% of adeps pro suppository (for example Witepsol 4) is melted, cooled to 35° C. and the mixture of active ingredient and lactose is mixed in it with homogenizator. The obtained mixture is mould in cooled forms.

f) Lyophilized Powder Ampoule Compositions:
A 5% solution of mannitol or lactose is made with bidistilled water for injection use, and the solution is filtered so as to have sterile solution. A 0.01-5% solution of the active ingredient is also made with bidistilled water for injection use, and this solution is filtered so as to have sterile solution. These two solutions are mixed under aseptic conditions, filled in 1 ml portions into ampoules, the content of the ampoules is lyophilized, and the ampoules are sealed under nitrogen. The contents of the ampoules are dissolved in sterile water or 0.9% (physiological) sterile aqueous sodium chloride solution before administration.

What we claim is:
1. A compound of the formula (I)

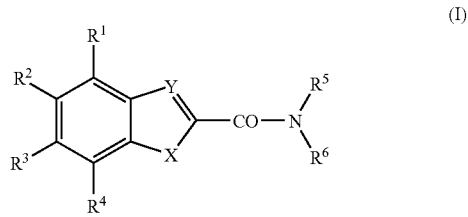

wherein
two of the neighboring $R^1$, $R^2$, $R^3$ and $R^4$ groups form an oxo-oxazolidine ring fused to the benzene ring of the indole nucleus,
and the other two of $R^1$, $R^2$, $R^3$ and $R^4$ groups are hydrogen atoms,
$R^5$ and $R^6$ together with the nitrogen between them form a saturated or unsaturated, 4-6 membered heterocyclic ring, which is substituted by phenoxy, phenyl-($C_1$-$C_4$ alkyl), phenyl-($C_1$-$C_4$ alkoxy), phenoxy-($C_1$-$C_4$ alkyl), or benzoyl, optionally substituted on the aromatic ring by one or more halogen atoms, cyano or hydroxy groups, $C_1$-$C_4$ alkyl or $C_1$-$C_4$ alkoxy groups, X is —NH—, Y is a —CH— group, or a pharmaceutically acceptable salt thereof formed with acids or bases.

2. A compound of the Formula (I) defined in claim 1 and selected from the group consisting of:
- 6-(4-benzylpiperidin-1-carbonyl)-1,5-dihydro-oxazolo[4,5-f]indole-2-one;
- 6-(4-benzyloxypiperidin-1-carbonyl)-1,5-dihydro-oxazolo[4,5-f]indole-2-one; and
- 6-[4-(4-fluorobenzyl)piperidine-1-carbonyl]-1,5-dihydro-oxazolo[4,5-f]indole-2-one;

or a pharmaceutically acceptable salt thereof formed with acids or bases.

3. 6-(4-benzylpiperidin-1-carbonyl)-1,5-dihydro-oxazolo[4,5-f]indole-2-one as defined in claim 1 or a pharmaceutically acceptable salt thereof formed with acids or bases.

4. A pharmaceutical compositions having an NR2B selective receptor antagonist effect, comprising a therapeutically effective amount of a compound of the Formula (I) as defined in claim 1 or a pharmaceutically acceptable salt thereof formed with acids or bases and a pharmaceutically acceptable inert carrier.

5. A method of treating pain in a mammalian subject in need of the treatment which comprises the step of administering to the mammalian subject a therapeutically effective amount of the compound of the Formula (I) defined in claim 1.

6. A process for preparing a compound of the Formula (I)

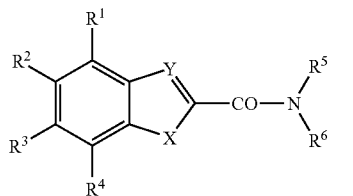

wherein two of the neighboring $R^1$, $R^2$, $R^3$, $R^4$ groups form an oxo-oxazolidine ring fused to the benzene ring of the indole nucleus, and the other two $R^1$, $R^2$, $R^3$, $R^4$ groups are hydrogen atoms, $R^5$ and $R^6$ together with the nitrogen between them form a saturated or unsaturated, 4-6 membered heterocyclic ring, which is substituted by phenoxy, phenyl-($C_1$-$C_4$ alkyl), phenyl-($C_1$-$C_4$ alkoxy), phenoxy-($C_1$-$C_4$ alkyl), or benzoyl, optionally substituted on the aromatic ring by one or more halogen atoms, cyano or hydroxy groups, $C_1$-$C_4$ alkyl or $C_1$-$C_4$ alkoxy groups, X is —NH—, Y is a —CH— group, or a pharmaceutically acceptable salt thereof formed with acids or bases, which comprises the step of:

amidating a compound of the Formula (II)

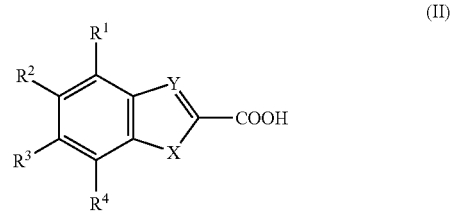

wherein the meaning of $R^1$, $R^2$, $R^3$, $R^4$, X and Y are as defined above with a compound of the Formula (III)

wherein the meaning of $R^5$ and $R^6$ are as defined above, to obtain the compound of the Formula (I) or a pharmaceutically acceptable salt thereof formed with an acid or a base, then the so obtained compound of Formula (I) or pharmaceutically acceptable salt formed with an acid or a base is optionally transformed into another compound of the Formula (I) or pharmaceutically acceptable salt thereof formed with an acid or a base by introducing a new substituent and/or by modifying or removing an existing substituent, and/or by forming a pharmaceutically acceptable salt with an acid or base and/or by liberating a compound of the Formula (I) from its pharmaceutically acceptable salt formed with an acid or base.

7. The process defined in claim 6, wherein the compound of the Formula (II undergoing amidation with the compound of the Formula (III), is in the form of an active derivative of a carboxylic acid.

8. The process defined in claim 7, wherein the compound of the Formula (II) in the form of an active derivative of a carboxylic acid is an ester formed with O-benzotriazol-1-yl-N,N,N',N'-tetramethyluronium hexafluorophosphate.

9. The process defined in claim 7, wherein the compound of the Formula (II) in the form of an active derivative of a carboxylic acid is an acid halogenide.

10. The process defined in claim 9, wherein the acid halogenide is an acid chloride.

* * * * *